United States Patent [19]

Kramer et al.

[11] Patent Number: 5,716,903
[45] Date of Patent: Feb. 10, 1998

[54] PREPARATION OF AMMONIUM GLYPHOSATE USING AQUEOUS AMMONIUM HYDROXIDE IN A LIQUID-SOLID REACTION SYSTEM

[75] Inventors: Richard M. Kramer, Chesterfield; Thomas M. Day, Creve Coeur; Ralph E. Lindemann, Jr., St. Louis; Jane L. Gillespie, University City, all of Mo.

[73] Assignee: Monsanto Company, St. Louis, Mo.

[21] Appl. No.: 778,890

[22] Filed: Jan. 3, 1997

Related U.S. Application Data

[63] Continuation of Ser. No. 472,152, Jun. 7, 1995, Pat. No. 5,614,468.

[51] Int. Cl.⁶ .................................................. A01N 57/02
[52] U.S. Cl. .................................................. 504/206
[58] Field of Search .................................................. 504/206

[56] References Cited

U.S. PATENT DOCUMENTS

| | | | |
|---|---|---|---|
| 4,840,659 | 6/1989 | Franz | 71/86 |
| 5,047,079 | 9/1991 | Djafar et al. | 71/86 |
| 5,070,197 | 12/1991 | Chin et al. | 544/11 |
| 5,266,553 | 11/1993 | Champion | 504/206 |
| 5,324,708 | 6/1994 | Moreno | 504/206 |
| 5,430,005 | 7/1995 | Kassebaum et al. | 504/206 |

FOREIGN PATENT DOCUMENTS

| | | |
|---|---|---|
| 0 394 211 | 4/1990 | European Pat. Off. . |
| 0 582 561 | 2/1994 | European Pat. Off. . |
| 2 692 439 | 5/1993 | France . |
| WO 87/04595 | 8/1987 | WIPO . |
| WO 90/07275 | 7/1990 | WIPO . |
| WO 92/12637 | 8/1992 | WIPO . |
| WO 94/10844 | 5/1994 | WIPO . |

*Primary Examiner*—S. Mark Clardy
*Attorney, Agent, or Firm*—Monsanto Company; Arnold, White & Durkee

[57] ABSTRACT

Solid N-phosphonomethylglycine or glyphosate acid is charged to a substantially closed system and then partially pre-dried as by continuously recirculating it through a hot air grinding/drying system. A cooled solution of ammonium hydroxide is then metered into and reacted with the partially dried glyphosate acid as it is being recirculated in a manner such that the moisture content of the reaction mass so formed is continuously decreased throughout the reaction. Following completion of the ammonium hydroxide addition, a powdered reaction mass/product having a moisture content of about 2 wt. % is formed. Significantly, at this stage, the ammonium glyphosate product is suitable for end use and it can be readily dissolved in water and immediately used as a herbicide or plant growth regulator. More importantly, however, this product is capable due to its highly sorptive character to be further formulated into a product exceptionally highly loaded with adjuvants and particularly surfactants.

15 Claims, 1 Drawing Sheet

PREPARATION OF AMMONIUM GLYPHOSATE USING AQUEOUS AMMONIUM HYDROXIDE IN A LIQUID-SOLID REACTION SYSTEM

This is a continuation of application Ser. No. 08/472,152 filed Jun. 7, 1995; now issued as U.S. Pat. No. 5,614,468.

BACKGROUND

1. Field of the Invention

This invention relates to a dry, non-clumping herbicidal composition together with a method for making the composition. More particularly, the present invention relates to an ammonium glyphosate herbicide and an efficient method for making solid ammonium glyphosate products that readily dissolve in water and that can be used to prepare highly-loaded, adjuvant-containing dry/solid glyphosate compositions.

2. Description of the Related Art

N-phosphonomethylglycine [$HOOCCHSNHCH_2NHCH_2PO(OH)_2$], which is commonly referred to as glyphosate acid or simply glyphosate, is well known in the art as a highly effective herbicide. It is also known that glyphosate, an organic acid, has relatively low solubility in water. Thus, glyphosate is typically formulated as a water-soluble salt, particularly as the mono-isopropylamine (IPA) salt to kill or control weeds or plants. Glyphosate is sold commercially as an aqueous concentrate in the form of its IPA salt by Monsanto Company of St. Louis, Mo. (U.S.A.) under the registered trademark Roundup®.

Various salts of glyphosate, methods for preparing salts of glyphosate, formulations of glyphosate and methods of use for killing and controlling weeds and plants are disclosed in U.S. Pat. Nos. 3,799,758 and 4,405,531 issued to John E. Frans on Mar. 26, 1974 and Sep. 20, 1983 respectively. Other U.S. Patents which disclose salts of glyphosate include U.S. Pat. No. 4,315,765 issued to George B. Large on Feb. 16, 1982, U.S. Pat. No. 4,507,250 issued to Izak Bakel on Mar. 26, 1985, U.S. Pat. No. 4,397,676 issued to Izak Bakel on Aug. 9, 1983, U.S. Pat. No. 4,481,026 issued to Michael P. Prisbylla on Nov. 6, 1984 and U.S. Pat. No. 4,140,213 issued to Erhard J. Prill on Feb. 20, 1979. All of the foregoing patents, in their entireties, are herein incorporated by reference.

Roundup® brand herbicide is sold as a water-soluble liquid concentrate. However, efforts have recently been made in the art to develop a water-soluble dry/solid glyphosate formulation which has the equivalent efficacy of Roundup®. Conventional reasons underlying these efforts have been desired cost savings in connection with the packaging, shipment and storage of a solid formulation versus a liquid. As can be appreciated, aqueous concentrates include a significant amount of solvent that adds to the size and weight of packaging containers and increases costs associated with post-manufacture delivery of the product to market.

A less readily apparent benefit also resides in the advantage of making a water-soluble, dry glyphosate. Namely, a granular formulation is believed to provide superior handling characteristics (i.e. controlled spillage) and is expected to be substantially lighter and less awkward to transport (and often hand carry) thereby making the product better suited for use in remote geographic locations.

Making a solid granular glyphosate formulation, however, entails overcoming inherent disadvantages relating principally to the increased production cost and comparative complexity of compounding a solid product from a combination of liquid and solid reactants rather than making a product in solution from the same reactants.

Several methods for making a solid water-soluble glyphosate salt-containing composition are known. For example, in U.S. Pat. No. 5,047,079 which issued on Sep. 10, 1991 to Djafar, there is disclosed a method for preparing a phytotoxic composition comprising ad mixing highly hygroscopic iso propylamine salt of glyphosate acid with a molten surfactant to form a matrix, the surfactant being a solid at ambient temperatures.

In U.S. Pat. No. 5,070,197 which issued on Dec. 3, 1991 to Chin, at. al. an extrusion method is disclosed in which a Bronsted acid, N-phosphonomethylglycine for example, is intimately admixed with sodium hydroxide in an extruder to produce a granular extrudate having a residual moisture content of no greater than 10%. Another method involving the production of a dry sodium glyphosate composition, albeit not involving extrusion, is disclosed in PCT application Publication No. WO 87/04595.

In U.S. Pat. No. 5,266,553 which issued on Nov. 30, 1993 to Champion, at. al. there is disclosed a method for preparing a dry, water-soluble salt of bentazon or of a herbicide containing a carboxylic acid functionality which involves repeated treatments of the salt with a neutralizing base selected from the group consisting of ammonia, an alkylamine, a hydroxyalkylamine, an alkaline salt of an alkali metal and combinations thereof.

In French Patent Publication No. 2,692,439 which was filed on May 19, 1993 and is assigned to Productos Osa SACIFIA, there is generally described a phytotoxic preparation comprising the monoammonium salt of N-phosphonomethylglycine as a powder or granule in combination with a wetting agent, surfactant and/or a pulverulent additive. As exemplified in the reference, the monoammonium salt is derived from reacting glyphosate acid with ammonium bicarbonate.

U.S. Pat. No. 5,324,708 which issued on Jun. 28, 1994 to Moreno, et. al. discloses a composition and related methods for-preparing and using a non-hygroscopic monoammonium glyphosate salt such as the mono-isopropylammonium salt of N-(phosphono-methyl)-glycine and the mono-isopropylammonium salt of (3-amino3-carboxypropyl)-methane phosphonic acid in dry powder form [sic].

In PCT application Publication No. WO 94/10844, published on May 26, 1994, a dry glyphosate composition is disclosed in which N-phosphono-methylglycine is admixed with, inter alia, an inorganic or organic, non-caustic base material such as diammonium phosphate or a basic guanidine salt such as guanidinium acetate.

EPO application Publication No. 0 394 211 which was published on Oct. 24, 1990, discloses an invention comprising a dry pesticidal composition and related methods for use and production. More particularly, the invention relates to the enhanced solubility of the pesticidal composition as achieved by the addition of an effective amount of an organosilicone block copolymer or a fluorocarbon wetting agent.

In PCT application Publication No, WO 90/07275 which was published on Jul. 12, 1990, there is disclosed an invention by which granular, water-soluble glyphosate compositions are made as by admixing, pan granulation, drying, spraying and extrusion.

In PCT application Publication No. WO 92/12637, which was published on Aug. 6, 1992, there is disclosed an invention relating to a dry, water soluble glyphosate including a composition comprising substantially nonreacted glyphosate, an acid acceptor such as sodium acetate and a liquid or solid surfactant.

All of the foregoing patents and publications are herein incorporated by reference.

The related art, as described, indicates that considerable effort has been directed toward formulating compositions and related methods for making and using dry glyphosates. However, none of the above-identified references discloses a practical method for producing a dry, water-dispersible, water-soluble and appreciably non-hygroscopic ammonium glyphosate composition which is capable of absorbing/adsorbing an exceptionally high level of adjuvants from N-phosphonomethylglycine and relatively inexpensive aqueous ammonium hydroxide on a manufacturing scale at an acceptable cost.

Thus, a need unsatisfied by known technology exists within the art for the present invention which accomplishes these and other objectives.

SUMMARY OF THE INVENTION

The unresolved needs of the art are satisfied by the present invention Which provides a highly desirable ammonium glyphosate dry plant growth regulator/herbicide composition and novel method for producing the composition whereby the disadvantages associated with known dry compositions and related methods, as discussed, are overcome through heretofore unknown and undisclosed limitations.

In accordance with the present invention glyphosate acid is charged to, as for example, a suitable blender such as a ribbon blender where it is blended and then, if necessary, partially pre-dried by recirculation through a hot air grinding/drying system.

While the acid is being continuously recirculated, a solution of cooled ammonium hydroxide is added, as by spraying, at a particular and critical rate to react with the acid. After a specified amount of ammonium hydroxide has been added, the reaction mass/product of the reaction, which is in the form of a powder, is suitable for end use as a herbicide or as a plant growth regulator.

In addition, and perhaps more importantly, the powdered reaction product due to its highly sorptive character is capable of being further formulated to absorb/adsorb an exceptionally high level of an adjuvant such as a wetting agent, an anti-foaming agent and particularly a surfactant composition. Thus, when so formulated, a very useful and highly desirable adjuvant-loaded product is formed which is every bit as good and effective as comparable products obtained by prior art processes which require more expensive starting materials.

Optionally, the powdered reaction product or the adjuvant-loaded product may be granulated to provide a free-flowing (i.e. non-caking), substantially dust-free and water soluble ammonium glyphosate herbicide and/or plant growth regulator.

Still further optional procedures may be carried out using the powdered reaction product. For example, the powder may be further ground and/or dried prefatory to packaging. Significant advantages achieved by the present invention reside in its relative simplicity, comparative low cost and in the fact that no highly specialized equipment is required to practice the invention. Thus, where conventional blending and milling/grinding equipment already exist, the present invention can be carried out efficiently on a commercial scale to produce a very high quality dry ammonium glyphosate product.

DETAILED DESCRIPTION OF THE PREFERRED EMBODIMENT

Figure 1:
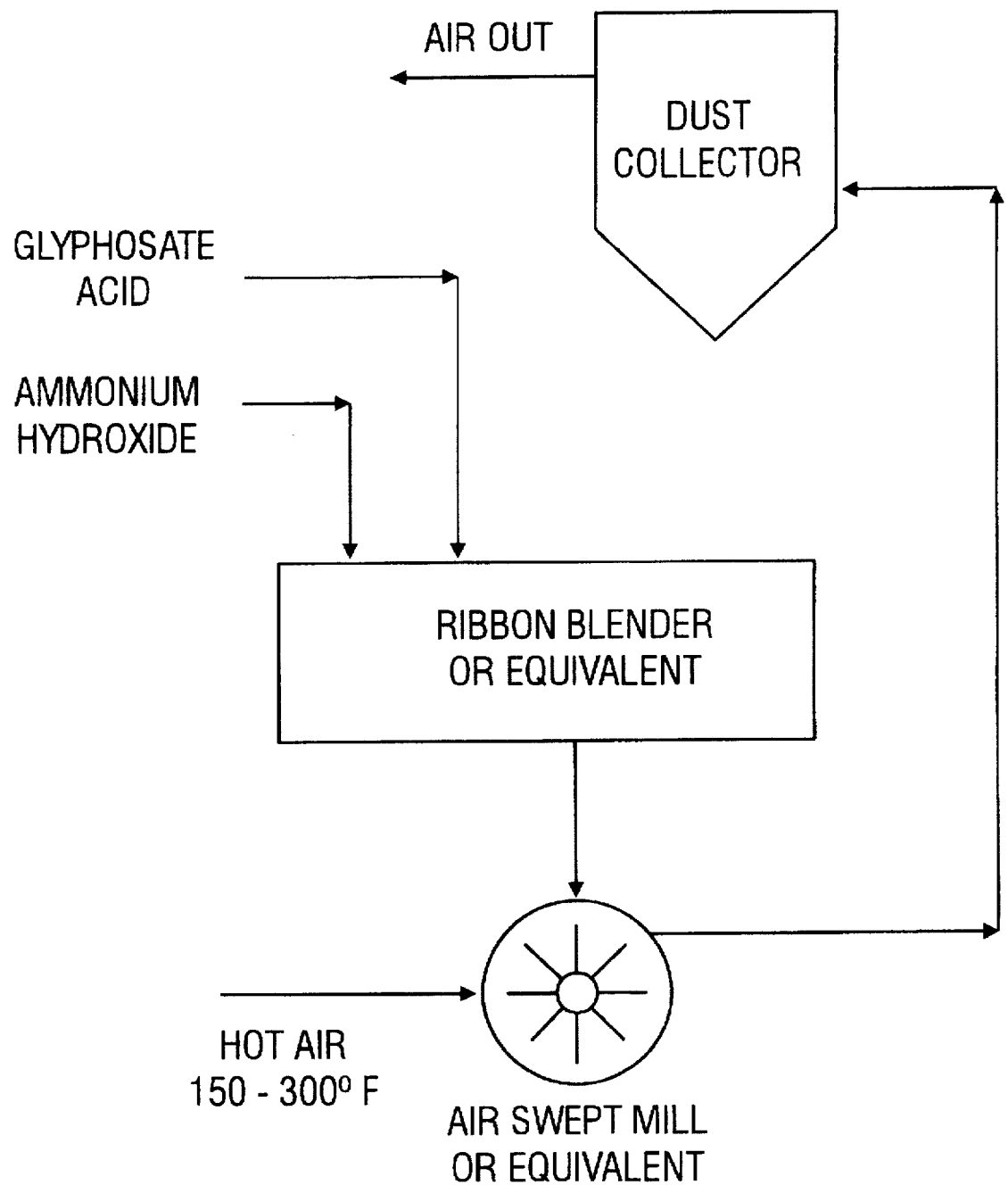
FIG. 1 is a schematic diagram illustrating the process for preparing dry ammonium glyphosate in accordance with the present invention.

The present invention relates to a novel method for reacting N-phosphonomethylglycine (glyphosate acid) with ammonium hydroxide to produce ammonium glyphosate powder, a key raw material which may be used as is or in granulated form or as a starting material in the formulation of a granulated surfactant-loaded dry glyphosate composition.

Until now, a comparatively inexpensive, effective and practical method for producing dry ammonium glyphosate powder which is capable of being further formulated to absorb/adsorb an exceptionally high level of an adjuvant using aqueous ammonium hydroxide has not been known.

Instead, various alternate and less advantageous methods have been developed by which ammonium glyphosate as well as alkali metal glyphosates such as sodium glyphosate have been made in dry, powder form. For example sodium glyphosate has been produced by reacting glyphosate acid with sodium acetate or by extruding the acid with sodium hydroxide as described above in PCT application Publication No. WO 92/12637 and U.S. Pat. No. 5,070,197 respectively.

Sodium glyphosate granules and powders have, until now, provided satisfactory dry glyphosate compositions. However, when compared to ammonium glyphosate salt compositions, the sodium salt is much more hygroscopic meaning it is not as resistant against ambient humidity. Thus, the sodium glyphosate salt is considered more difficult and more expensive to process as a dry composition and, once formed as such, it has a greater tendency to agglomerate which results in undesirable "caking" of the finished material.

Also, due to the relative molecular weights of ammonia and sodium, sodium glyphosate salt compositions have a lower concentration of the active glyphosate than their counterpart ammonium glyphosate compositions. In addition, the per pound cost of sodium cation is much more expensive than the cost of obtaining the ammonium cation. The comparative disadvantages of sodium glyphosate compositions are, thus, apparent.

As previously noted, certain solid/solid reaction methods are known for making dry ammonium glyphosate. Reacting ammonium bicarbonate with glyphosate acid, for example, as described above in French Publication No. 2,692,439 is believed to yield a dry ammonium glyphosate composition.

The invention disclosed herein, however, constitutes an advance in the art of making dry ammonium glyphosate even over known methods utilizing ammonium bicarbonate.

For example, in practicing the present invention which involves reacting liquid ammonium hydroxide with solid N-phos-phonomethylglycine, it has been observed that the per pound cost of obtaining ammonium cation derived from ammonium bicarbonate is approximately ten to twenty times more expensive than the per pound cost of obtaining an equivalent amount of the same cation from ammonium hydroxide. In the large-scale commercial production of ammonium glyphosate, this cost differential alone strongly militates in favor of an effective method, such as that disclosed herein, for producing a solid ammonium glyphosate using ammonium hydroxide as the source of ammonium cation.

As used herein the terms "solid" and/or "dry" mean the physical state in which the formulation has a specific shape and volume and resists deformation. The solid may take the form of pellets, flakes, granules, powder or the like. Further, it will be understood that the solid formulation may subsequently be dissolved in a suitable diluent, usually and preferably water, and applied to the locus where plant regulation or eradication is desired as by spraying or other conventional means.

From a technical perspective, the simple admixture of N-phosphonomethylglycine in commercially standard "wet cake" form (i.e. having a moisture content of approximately 6–20 wt. %) with liquid ammonium hydroxide in stoichiometric quantities yields a viscous, "dough-like" product that is not compatible with conventional equipment for further processing. Such a product has a physical character wholly distinct from the product generated by the process of the present invention. Thus, adherence to the process of the present invention and the manner and extent to which the reaction between the glyphosate acid and the ammonium hydroxide is controlled in accordance with the process, are critical in ensuring the creation of a solid, free-flowing (i.e. non-caking) and water soluble ammonium glyphosate salt which, importantly, is capable of being further formulated to absorb/adsorb an exceptionally high level of adjuvants such as surfactants.

In accordance with the process of the present invention, the reactant mixture is continuously dried and conditioned to maintain a suitable moisture content throughout the step of ammonium hydroxide addition such that a free-flowing, readily handleable, powder is generated. This not only allows processing in conventional equipment, but also produces an ammonium glyphosate powder that can be used to make dry glyphosate products highly-loaded with adjuvants.

The inventors have determined that the moisture content in the reaction mass during the ammonium hydroxide addition to the glyphosate acid is a critical aspect of the invention.

The amount of ammonium hydroxide which is required in order to practice the invention is equivalent to that amount which is required to achieve approximately 95–105% neutralization of the acid which can be determined by conventional analytical methods known to those ordinarily skilled in the art such as by pH measurement.

In accordance with the process of the present invention, the wet cake is charged to an actuated and suitable conventional blender. A pre-determined quantity of sodium sulfite may be added to prevent the possible formation of nitrosamines. Although the addition of sodium sulfite is not necessary to practice the invention and does not affect the reaction between the glyphosate acid and ammonium hydroxide, certain governmental regulations require that nitrosamine levels in products of this nature be below 1 ppm. Experience has shown that, when added, the effective range of sodium sulfite to be added as ensurance against the presence of unacceptable levels of nitrosamines is between 0.2 and 1.0 wt. % of the dried, finished product.

A pre-drying step, if required, occurs next during which the wet cake and, if desired, sodium sulfite are continuously circulated through a hot air drying and milling system which is arranged in communication with the blender. A constant and elevated drying air temperature of about 170 to 300 degrees Fahrenheit, and preferably 250° to 270° F., is maintained and the mixture is continuously circulated until its total moisture content is below about 6 wt. %. To determine the existence of this condition, a sample of the mixture is then recovered and assayed. If the moisture content of the wet cake starting material is already below about 6 wt. %, then the pre-drying step is unnecessary.

Next, the temperature of the drying air system is substantially reduced to a temperature of about 150 to 200 degrees Fahrenheit as the mixture continues to circulate. A cooled solution of ammonium hydroxide is then added to the mixture, as by spray application into the blender, to form an ammonium glyphosate reaction mass. A standard commercial ammonium hydroxide solution is employed; preferably one that contains approximately 29 wt. % ammonia. The solution is first cooled to about 40 to 50 degrees Fahrenheit because it is known that liquid ammonium hydroxide is volatile and that it boils at 86 degrees Fahrenheit. Thus, ammonium hydroxide loss is controlled and the likelihood of atmospheric pollution by the evaporating solution is reduced.

The manner and rate at which the ammonium hydroxide is introduced are very significant. Preferably, the solution is sprayed, as by one or more nozzles into the blender containing the wet cake and sodium sulfite, if present, using a coarse spray. The flow of the sprayed solution is metered such that the moisture content of the reaction mass consistently decreases from the initial concentration of circa 6 wt. % down to about 2 wt. % (i.e. loss of weight on drying or LOD) or less during the period in which the ammonium hydroxide is added and the exothermic reaction proceeds.

Under the process conditions specified, the ammonium hydroxide spray rate is designed in such a way as to control the rate at which water is introduced with the ammonium hydroxide and formed as a product of the reaction between the glyphosate acid and the ammonium hydroxide. The object is to introduce the water at a rate slower than the rate at which moisture is being driven from the wet cake/sodium sulfite mixture due to the circulating dryer system.

Other ammonium hydroxide addition rates were experimented with but did not yield the highly desirable product generated by the present invention. For example, when the ammonium hydroxide was introduced under the same process conditions but at a 40% higher rate, the ammonium glyphosate powder produced had less sorptive capacity rendering it unfit for further processing such as loading with adjuvants and particularly with surfactants. Addition rates in excess of the 40% higher rate have an immediate adverse effect on the physical characteristics of the reaction mass the reaction mass becomes a very wet and "dough-like" cohesive mass rendering it unsuitable for completion of the process.

Also, for example, if the glyphosate acid and sodium sulfite mixture is not pre-dried to below about 6 wt. %, the material in the blender again also becomes very wet and "dough-like" rendering it unsuitable for use in completing the process.

It is appreciated that the pre-drying step may be avoided or abbreviated such that the moisture content in the mixture of glyphosate acid and sodium sulfite may be initially greater than about 6 wt. %. However, it is also known that the ammonium hydroxide addition rate under such circumstances would be so slow as to render the process economically unfeasible.

As the process proceeds, samples should periodically be obtained and assayed to measure the moisture content to ensure that the rate of water removal from the reaction is greater than the rate at which water is being added. This can simply be determined by observing progressive decreases in the moisture content of the mixture.

The above-described process conditions should be maintained until all of the ammonium hydroxide has been added. At this point, the ammonium glyphosate is in the form of a powdered product which may be further processed. Such further processing may include: the addition of sodium sulfite, grinding, drying, granulating or formulating with adjuvants.

The decision regarding which, if any, of these further processes is to be performed is dictated, largely, based upon the intended end-use of the product.

Regardless of the further processing selection, however, a quantity of sodium sulfate may be again optionally added. In conjunction with this step, the reaction mass may be further ground to make it more suitable for further processing. If further processing such as granulation or formulation with adjuvants is to be performed immediately, it is not necessary to further dry the product at this stage. However, if the product is to be shipped or stored for more than a few days, for example, then it should be further dried to less than 1 wt. % moisture at this time to prevent caking.

Where it is desired to use the product without the addition of any adjuvants as a herbicide or plant growth regulator, then it is desirable to granulate or agglomerate it, such as by pan granulation and drying or by other methods known in the art.

Should it be desirable to produce a product containing adjuvants such as surfactants, anti-foaming agents, wetting agents and the like, these may be added as by blending in suitable equipment and, preferably, by kneading, extruding and drying or as by other methods well-known to the ordinarily skilled artisan.

The following example illustrates production of the composition of the invention in accordance with the process described herein. All percentages are based upon weight, unless otherwise clearly indicated.

EXAMPLE 1

In a plant-scale reactor system comprised of a stainless steel ribbon blender, a suitable hot air drying system such as an air-swept hammer mill supplied with hot air and an adapted dust collector, all of which were in communication with each other as by suitable connecting conduits, 2400 lbs. of standard grade N-phosphonomethylglycine "wet cake" having an assayed moisture content of about 10% LOD was charged to the ribbon blender where it was immediately mixed.

Once all of the wet cake had been deposited in the ribbon blender, 4.8 lbs. of solid sodium sulfite was also charged to the blender and combined with the wet cake whereupon it was intimately mixed. The combination of wet cake and sodium sulfite was then circulated within the hot air-swept mill system using an air inlet temperature of about 250° F. for one hour. A sample of the mixture was then recovered and assayed to determine its moisture content/ LOD.

When the moisture content of the mixture was reduced to approximately 6%, the material continued to be circulated through the drying system and the air inlet temperature to the mill was reduced to about 170° F.

With the air temperature within the system being maintained at about 170° F., a solution of ammonium hydroxide (29% $NH_3$), previously cooled to a temperature of between 40 to 50° F., was then pumped to the ribbon blender and coarsely sprayed by five adjustable nozzles onto the glyphosate acid to form a reaction mass. A total quantity of 730 lbs. of liquid ammonium hydroxide was introduced by spraying. A rate not exceeding 3.5 lbs./minute was established for feeding the liquid ammonium hydroxide.

During the approximately 3.5 hours that were required to feed all of the ammonium hydroxide solution, several samples of the circulating mixture were obtained and assayed to ensure that the rate of ammonium hydroxide addition provided for the progressive reduction of the total moisture content of the reaction mass. At the conclusion of the ammonium hydroxide addition, the reaction mass was a free-flowing powdered product particularly well-suited for immediate and desirable further processing.

In the process which gave rise to this Example 1, it was intended that the reaction mass be further processed at a later time. In view of this fact, the reaction mass was, at this point, conditioned in such a way as to ensure that it would not cake during storage. First, however, an additional and equal quantity of sodium sulfite was charged to the blender and mixed for approximately ten minutes to ensure uniform dispersion with the powdered reaction mass.

This combination was next physically comminuted by passing the dry powdered composition through an air classifying mill to reduce the discrete particles of the composition to a substantially small and uniform size. Although the air classifying mill was used because it happened to be a part of the equipment train used for this Example 1, this milling procedure is not required to practice the invention.

Following comminution, the product was subjected to conventional fluid bed drying to ensure that the resulting finished product exhibited a residual moisture content of no greater than 1.0% LOD.

From the starting materials which included 2400 lbs. of glyphosate acid (i.e. "wet cake" containing about 10% moisture), a total of 9.6 lbs. of sodium sulfite (optionally) and 730 lbs. of liquid ammonium hydroxide, a theoretical product yield of 2394 lbs. of dry, powdered ammonium hydroxide having a residual moisture content of approximately 0.5% can be obtained.

In addition to possessing highly desirable commercial product qualities, the product obtained in connection with the foregoing example has demonstrated excellent storage and stability characteristics. In fact when stored properly, as for example in sealed polyethylene bags, the product has proven not to degrade or cake after more than six months of actual warehousing.

As discussed in some detail above, the powdered reaction mass/product produced in accordance with the novel process of this invention is particularly well adapted to be further formulated to absorb/adsorb high levels of adjuvants.

In combination, the relative simplicity of the present invention, its ability to be practiced using conventional equipment and the comparative low cost of the ammonium cation furnished by ammonium hydroxide deem very significant the capacity of the powdered reaction mass/product to absorb/adsorb high levels of adjuvants.

While the choice of a particular adjuvant or combination of adjuvants will be easily made by those ordinarily skilled in the art without undue experimentation, Example 2 presented below illustrates the exceptional sorptive capacity of the powdered reaction mass/product when loaded with surfactant.

EXAMPLE 2

The powdered reaction mass/product formed by the process described in Example 1 can be used to make a dry formulation of ammonium glyphosate containing a high level of surfactant of at least about 20 wt. %.

To make such a highly loaded product, 16 kilograms of the powdered reaction mass/product is blended with 4 kilograms of a polyoxyethylene alkylamine surfactant and 1.4 kilograms of water in a jacketed batch kneader, such as a Fuji Paudal, for approximately 10 minutes with water at a temperature of about 80° C. circulating in the jacket. The dough hat is formed is then extruded, as for example in a Fuji Paudal twin screw extruder, fitted with screens having approximately 2 mm. diameter borings. The extrudate obtained consisted of discrete, "spaghetti-like" short noodles which did not stick together and which were easily and conveniently dried, such as for example in a Fitz-Aire fluid bed dryer, without formation of undesirable lumping.

To illustrate the significance of the process of the present invention as it pertains to the sorptive character of the powdered reaction mass/product, a product made in accordance with all of the process variables of the invention but, wherein the addition rate of ammonium hydroxide solution was 40% higher, a doughy product was produced that was undesirably wet and sticky to touch. Further, the extrudate produced therefrom consisted of-undesirably "spaghetti-like" noodles that stuck together and formed large agglomerates. This extrudate was very difficult to fluidize in the fluid bed dryer and resulted in the formation of a large quantity of dried agglomerates which, in order to be usable, would then have to be ground and recycled back through the extrusion process.

What we claim is:

1. A method for preparing a dry ammonium N-phosphono-methylglycine phytoactive composition capable of being highly loaded with one or more adjuvants which comprises reacting aqueous ammonium hydroxide with N-phosphonomethylglycine in a conventional reactor system to form a reaction mass such that the moisture content of said reaction mass is continuously decreased throughout the reaction.

2. The method of claim 1 further comprising the step of drying said N-phosphonomethylglycine prior to reacting it with said ammonium hydroxide.

3. The method of claim 1 wherein said ammonium hydroxide and said N-phosphonomethylglycine are reacted in approximately equivalent molar amounts.

4. The method of claim 1 wherein the reaction is carried out in conventional blending equipment such as in a ribbon blender.

5. The method of claim 1 wherein the moisture content of said reaction mass is continuously decreased throughout the reaction by circulating said reaction mass through an air swept mill or equivalent using air heated to a temperature of about 150° F. to about 300° F.

6. The method of claim 2, wherein said drying is accomplished by circulating said N-phosphonomethylglycine through an air swept mill system or equivalent using air heated to a temperature of about 230° F. to about 280° F.

7. The method of claim 1 wherein said ammonium hydroxide is any commercially available aqua ammonia solution.

8. The method of claim 1 wherein the moisture content of said N-phosphonomethylglycine is within the range of about 7 wt. % to about 20 wt. %.

9. The method of claim 1, wherein the air is heated to a temperature within the range of about 150° F. to about 200° F.

10. The method of claim 1 wherein said moisture content of said reaction mass is less than approximately 2 wt. % at the conclusion of said reaction.

11. The method of claim 2, wherein the molar ratio of ammonia to N-phosphonomethylglycine in said reaction mass is approximately 0.95:1.0 to 1.05:1.0.

12. The method of claim 2 wherein said reactor system comprises at least a conventional blender and hot air dryer and wherein said N-phosphonomethylglycine is dried by circulation through said reactor system which is heated to about 250° F. to about 280° F. until its moisture content is reduced to about 6 wt. % or below.

13. The method of claim 2 wherein said ammonium hydroxide solution is an aqueous solution containing approximately 29 wt. % ammonia cation.

14. The method of claim 1 further comprising blending the reaction mass with surfactant to form a dough, extruding the dough into short noodles, and drying the noodles.

15. The method of claim 1 further comprising:

drying the reaction mass to a moisture content of less than about 1 wt %;

optionally milling or granulating the dried reaction mass;

blending the dried reaction mass with surfactant to form a dough; and extruding the dough into short noodles.

* * * * *